United States Patent [19]
Yokoyama et al.

[11] Patent Number: 5,304,529
[45] Date of Patent: *Apr. 19, 1994

[54] SYNERGISTIC MIXTURE OF BIOREGULATOR COMPOUNDS AND METHOD OF THEIR USE

[75] Inventors: Henry Yokoyama; James H. Keithly, both of Pasadena, Calif.; Harold W. Gausman, Amarillo, Tex.

[73] Assignees: Tropicana Products, Inc., Bradenton, Fla.; The United States of America as represented by the Secretary of Agriculture, Washington, D.C.

[ * ] Notice: The portion of the term of this patent subsequent to Mar. 29, 2011 has been disclaimed.

[21] Appl. No.: 954,725

[22] Filed: Sep. 30, 1992

Related U.S. Application Data

[63] Continuation-in-part of Ser. No. 860,413, Mar. 30, 1992, and a continuation-in-part of Ser. No. 954,726, Sep. 30, 1992.

[51] Int. Cl.$^5$ .............................................. A01N 33/08
[52] U.S. Cl. .................................... 504/148; 504/326
[58] Field of Search ................. 504/326, 148; 564/340, 564/346

[56] References Cited

U.S. PATENT DOCUMENTS 4,204,859  5/1980  Yokoyama ............................ 71/121
4,363,188  12/1982  Dastoor ................................ 71/86 X

OTHER PUBLICATIONS

Harold W. Gausman, John D. Burd, Jerry Quisenberry et al. Bio/Technology vol. 3–Mar., 1985.
Henry Yokoyama, Charles DeBenedict, Wan–Jean Hsu et al. Bio/Technology–Mar., 1984.
J. H. Keithly & H. Yokoyama et al. Plant Growth Regulation 9: 19–26, 1990 Kluwer Academic Publishers Printed in Netherlands.
H. Yokoyama and J. H. Keithly–ACS Symposium Series No. 405 Quality Factors of Fruits and Vegetables: Chemistry Technology Copyright 1989 by the American Chemical Society.
James H. Keithly, Hideaki Kobayashi and Henry Yokoyama PGRSA Quarterly 1990 18(2):55–61.
Ernest Hayman, Henry Yokoyama and Seth Gold Journal of Agricultural & Food Chemistry, Mar./Apr. 1987, 186–188, by the American Chemical Society.
Ernest P. Hayman and Henry Yokoyama HortScience 25(12): 1614–1615, 1990.
Wan–Jean Hsu, Charles DeBenedict, Steve D. Lee et al. Jrl. of Agricultural & Food Chemistry, Jan./Feb. 1989, 12–14, by the American Chemical Society.
Wan Jean Hsu and Henry Yokoyama Agricultural & Food Chemistry, Jan., 1991, 96–98 by the American Chemical Society.
H. Yokoyama, S. Gold C. DeBenedict and B. Carter Food Technology 40(11) 111–113, Nov. 1986.
Stephen M. Poling, Wan–Jean Hsu and Henry Yokoyama Phytochemistry, vol. 21, No. 3, pp. 601–604, 1982.
Stephen M. Poling, Wan–Jean Hsu and Henry Yokoyama Phytochemistry, vol. 14, pp. 1933–1938 Paragon Press Printed in England, 1975.
Hideaki Kobayashi, James H. Keithly and Henry Yokoyama (J. Japan. Soc. Hort. Sci.) 59(1): 115–119. 1990.
W.–J. Hsu, H. Yokoyama and C. DeBenedict Phytochemistry, vol. 29, No. 8, pp. 2247–2251, 1990 Printed in Great Britain.

*Primary Examiner*—Richard L. Raymond
*Assistant Examiner*—B. Bembenick
*Attorney, Agent, or Firm*—Kane, Dalsimer, Sullivan, Kurucz, Levy, Eisele & Richard

[57] ABSTRACT

This invention is directed to a synergistic mixture of bioregulator compounds and a method of their use. Mixtures of these compounds, when applied to plants in bioregulatory amounts, enhance important plant properties such as sugar content, essential oils, vitamin C, proteins, and an overall increase in total plant biomass. The treated plants exhibit accelerated ripening, improved color scores of juice products, and an accelerated maturation. The bioregulator compounds which comprise the invention enhance these plant properties when applied individually to plants, but the application of mixtures of such compounds effect a greater than additive result and enhance the aforementioned plant properties to an unpredicted and unexpected degree when compared to known bioregulator agents.

23 Claims, 2 Drawing Sheets

SYNERGISTIC MIXTURE OF BIOREGULATOR COMPOUNDS AND METHOD OF THEIR USE

This application is a continuation-in-part of presently pending U.S. application Ser. No. 860,413 filed on Mar. 30, 1992 pending, and application Ser. No. 954,726 filed on Sep. 30, 1992 pending the disclosure of that application is incorporated herein by reference.

FIELD OF THE INVENTION

This invention is directed to a synergistic mixture of bioregulator compounds and a method of their use. Mixtures of these compounds, when applied to plants in bioregulatory amounts, enhance important plant properties such as sugar content, essential oils, vitamin C, proteins, and an overall increase in total plant biomass. The treated plants exhibit accelerated ripening, improved color scores of juice products, and an accelerated maturation. The bioregulator compounds which comprise the invention enhance these plant properties when applied individually to plants, but the application of mixtures of such compounds effect a greater than additive result and enhance the aforementioned plant properties to an unpredicted and unexpected degree when compared to known bioregulator agents.

BACKGROUND OF THE INVENTION

Developments in agriculture have produced chemical compounds and methods for their application which function as plant bioregulators and thus serve to enhance one or more properties exhibited by the treated plant. For example, U.S. Pat. No. 3,671,219 discloses a quarternary ammonium compound which when applied to plants enhances the sugar content of sugar cane. U.S. Pat. No. 4,204,859 discloses that the addition of certain phenoxytrialkylamines enhance the hydrocarbon production of rubber in plants. U.S. Pat. No. 4,159,903 discloses a method for increase of polyisoprene production in rubber producing plants such as Guayule. U.S. Pat. No. 3,833,350 discloses that carotenoid accumulation in plants can be increased according to a method comprised applying compounds including (halogenated phenoxy) trialkylamines. U.S. Pat. Nos. 3,864,501, 3,911,148, and 3,911,152 disclose a method for increasing the carotenogenic pigments of fruits and vegetables which comprises the application of compounds including (methyl phenoxy) trialkylamine.

U.S. Pat. No. 4,797,153 discloses a method for increasing total plant biomass and individual plant constituents such as sugar, protein, lipid, and essential oils which comprises the application of certain substituted phenoxytrialkylamines and substituted phenylthiotrialkyl amines, or dialkyl morpholium halides. The compounds are applied in bioregulatory amounts to plant seeds, plant seedlings, or plant buds at the early stage of plant development, or to trees during a week before or after flower bud swell. It has since been shown that the application of the compounds of this reference in bioregulatory amounts affect the photosynthetic pathway in green plants in a manner which facilitates the assimilation of carbon dioxide in the photosynthetic pathway, thereby increasing the carbon atoms available for synthesis of total biomass and individual plant constituents.

SUMMARY OF THE INVENTION

The present invention is directed towards mixtures of the bioregulator compounds disclosed in pending U.S. application Ser. No. 860,413 and a method for the use of such mixtures. These bioregulator compounds are (benzyl substituted) trialkylamine ether compounds which when applied as mixtures to plants at specified levels increase important plant constituents, increase total plant biomass, and increase the rate of plant growth and reduce the time required to plant maturity. Pigment accumulation in vegetative and reproductive tissues is increased. In treated citrus, the fruit exhibits a reduced peel thickness. The mixtures are applied to the plants in bioregulatory amounts—that is, an amount sufficient to increase plant biomass and accelerate growth but insufficient to harm the plant. The compounds of the present invention are a mixture of at least two compounds selected from the group of chemical compounds having the structure:

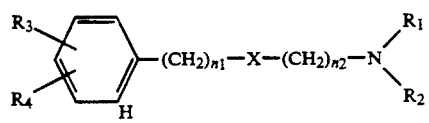

wherein X is either oxygen or sulfur, $R_1$ and $R_2$ are lower alkyl groups containing 1 to 6 carbon atoms, $n_1$ and $n_2$ are integers from 1 to 6, with $n_1$ and $n_2$ being independent of each other. $R_1$, $R_2$, $n_1$, $n_2$ may contain similar or dissimilar chemical structures.

$R_3$ and $R_4$ are independently hydrogen, chlorine, bromine, iodine, fluorine, lower alkyl groups containing 1 to 6 carbon atoms, lower alkoxy groups containing 1 to 6 carbon atoms, or condensed mono- and polycyclic aromatic ring systems, and wherein:

if $R_3$ and $R_4$ are 3,5-substituents, then the lower alkyl or alkoxy group must contain 3 to 6 carbon atoms; and wherein if $R_3$ is hydrogen, then $R_4$ must be a 4-substituent, with the proviso that $R_4$ is other than hydrogen; or b) an acid addition salt of the compounds defined above.

It has been found that the application of the mixtures of the invention causes the treated plants to form and store valuable plant constituents over untreated plants. The plants which have been treated with the bioregulatory mixtures of the invention have greater biomass than untreated plants resulting in increased crop production per unit area. Moreover, plants treated with these mixtures exhibit enhanced metabolic activity in forming and storing valuable plant constituents and in increasing plant-biomass when compared to plants treated with individual bioregulator agents, which is an unpredicted and unexpected result. The mixtures of the present invention exhibit a greater than additive effect when they are combined as bioregulatory agents and yield synergistic results relative to plants treated with individual bioregulator agents. The inventive mixtures provide a means for optimizing crop production per unit area with respect to the known state of the art.

In my co-pending U.S. application Ser. No. 860,413, it was shown that a compound disclosed therein known as N,N-diethylaminoethyl (4-methylbenzyl) ether (MBTA) is generally more effective as a plant bioregulator than the bioregulator compounds disclosed in U.S. Pat. No. 4,797,153. That is, MBTA treated plants exhibit a greater increase in total plant biomass and valuable plant constituents relative to dichlorophenoxytriethyl amine (DCPTA). A second compound disclosed in my co-pending application, N,N-diethylamino ethyl 3,4-dichlorobenzyl ether (DCBTA) performs comparably as a bioregulator with respect to the DCPTA. However, we have discovered that a mixture of DCBTA and MBTA, when applied to plants, effect an unpredicted and unexpected enhancement of plant metabolic activity in forming and storing valuable plant constituents and in increasing plant biomass with respect to similar treatments of individual bioregulator agents, including the DCPTA disclosed in U.S. Pat. No. 4,797,153 and the MBTA and DCBTA disclosed in our co-pending application Ser. No. 860,413. The mixture of MBTA and DCBTA, when applied to plants, results in a greater than additive bioregulatory effect when compared to treatments of the aforementioned individual bioregulator agents. These greater than additive, or synergistic effects, advance the state of the art further than the advancements disclosed in our co-pending application Ser. No. 860,413.

Detailed Description of the Preferred Embodiment

Figure 1B:
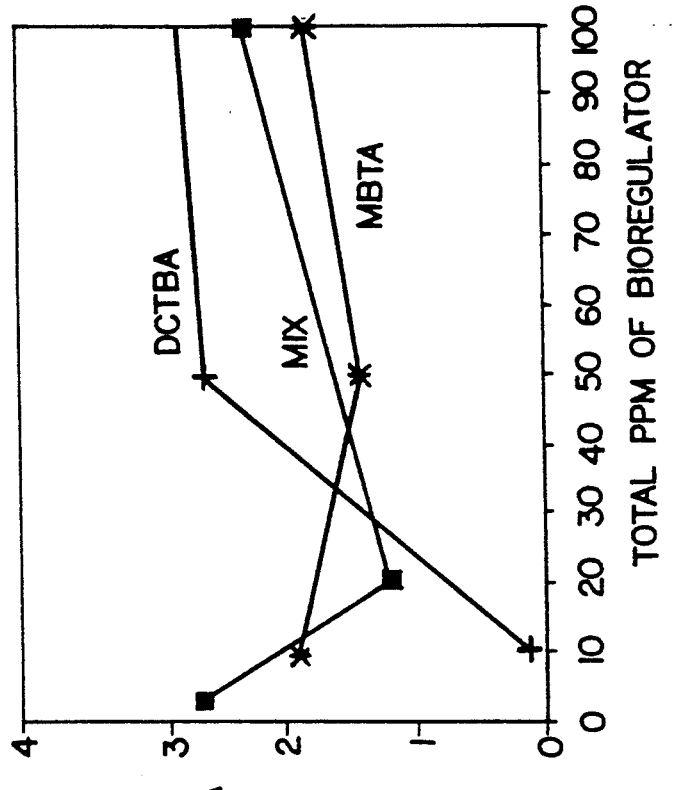
FIG. 1B shows the effect of a mixture of MBTA and DCBTA on Hamlin sweet orange juice BAR.

The benefits of the invention are obtained by applying any mixture of the following mixtures of compounds to plant seeds, seedlings, buds, or vegetative propagules. "Mixtures" as used herein, refers to a combination of at least any two compounds encompassed by this disclosure. Examples, by way of illustration and not limitation, of compounds suitable for use in the mixtures that can be used in the process of the invention are:

A. N,N-dialkylaminoalkyl 2,4-substituted benzyl ethers wherein the 2,4-substituents are independently chloro, bromo, iodo, methyl, ethyl, propyl, butyl, pentyl, hexyl, methoxy, ethoxy, propoxy, butoxy, pentoxy or hexoxy, and wherein the alkyl and dialkyl groups are independently methyl, ethyl, propyl, butyl or pentyl.

B. N,N-dialkylaminoalkyl 3,5-substituted benzyl ethers wherein the 3,5-substituents are independently chloro, bromo, iodo, methyl, ethyl, propyl, butyl, pentyl, hexyl, propoxy, butoxy, pentoxy or hexoxy, and wherein the alkyl and dialkyl groups are the same as those in A.

C. N,N-dialkylaminoalkyl 3,4-substituted benzyl ethers wherein the 3,4-substituents are independently chloro, bromo, iodo, methyl, ethyl, propyl, butyl, pentyl, hexyl, methoxy, ethoxy, proproxy, butoxy, pentoxy or hexoxy, and wherein the alkyl and dialkyl groups are the same as those in A.

D. N,N-dialkylaminoalkyl 4-substituted benzyl ether wherein the 4-substituent is either methyl, ethyl, propyl, butyl, pentyl, hexyl, methoxy, ethoxy, propoxy, butoxy, pentoxy or hexoxy, and wherein the alkyl and dialkyl groups are the same as those in A.

E. N,N-dialkylaminoalkyl (substituted naphthyl) ether wherein the alkyl and dialkyl groups are the same as those in A.

The preferred compounds of the present invention as set forth in groups A through E are those where $n_1$ and $n_2$ each are 2, X is oxygen, the dialkyl groups are di- methyl, the alkyl group is ethyl, and the benzyl substituents are 2,4-dichloro; 3,4-dichloro; 3-5-diisopropyl; 3,5,-ditertiary butyl; 3,4-dimethyl; 3,4-dimethoxy; 3-methyl, 4-methyl, 4-chloro or 3,4-naphthoxy.

It has been found that a mixture of two particular compounds are especially preferred in that plants treated therewith exhibit significant improvements in total plant biomass and individual plant constituents, with respect to plants treated with individual bioregulator compounds such as DCPTA, MBTA, and DCBTA. The particular mixture is of MBTA and DCBTA, and the mixture is further preferably comprised of an equal amount (1:1, w/w) of each of these compounds. However, use of unequal amounts of two or more bioregulators in mixture form does not limit the scope of the invention.

Various acid addition salts of the above disclosed compounds are easily produced, and mixtures thereof can be used as well. For example, by adding acid to the compounds of the invention, the following acid addition salts are formed:

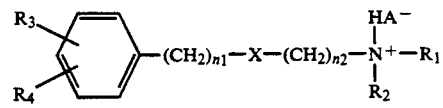

Wherein the molecular constituents are as set forth above, and wherein A is the anion derived from the acid added to the amine to form a salt. Mixtures of acid addition salts are comprised of two or more acid addition salts formed from the above compounds.

In order to achieve an increase in total biomass yield, enhanced plant nutrition or sensory quality, or to increase the rate of plant growth, the mixtures of the invention must be first applied to the plant at an early stage of development, that is, immediately prior to, or at the time when cell differentiation and plant growth are great. If application is made at a late stage of development some increase in yield or plant constituents may occur but not the significant increase which occurs where treatment is earlier. As a practical matter, treatment is made to the seed; to the post-emergent seedling plant, that is, to the plant at or prior to mid exponential vegetative growth, such as at the cotyledon, true leaf, two-leaf or four-leaf stage; or to trees during flower bud swell or a week before or after. For plants which are not grown from seed or do not produce flower buds such as vegetatively propagated plants like sugarcane, application should be at the developmental growth stages equivalent to the ones aforementioned. Since growth of the plant or tree dilutes the concentration of the bioregulatory mixture due to increase in plant biomass resulting in a biomass dilution effect, it may be desirable to apply more than one application subsequent to the initial one. Subsequent applications should be made before completion of cell differentiation of the growing plant or when applied to a growing tree before the completion of cell differentiation of the growing fruit.

The effective amount of the mixture to be applied so as to achieve the increase in biomass contemplated by the invention varies depending upon the stage of the plant's development when application is made, on whether the plant is grown in the field or greenhouse, the degree of penetration of the plant by the bioregulator, and whether or not a penetrating agent is used.

Generally, where the mixtures are applied to the seeds, the concentration is about 0.001 to 0.3 mg total of active ingredient per seed. Application is conveniently made by dissolving the mixture to be used in water at a concentration of 0.1 to 100 parts per million (ppm) in the diluent and soaking the seeds for about 2 to 6 hours. The concentrations described herein refer to the composite of bioregulatory agents comprising the mixture For example, 50 ppm refers to 50 ppm of total bioregulatory agents (eg: 25 ppm of DCBTA and 25 ppm of MBTA). As noted, it is preferred that the mixtures be comprised of equal amounts of each bioregulator agent in the mixture. Other means of treatment of seeds such as encapsulation of the seeds with the compounds by conventional methods are encompassed by the invention.

When application is made to the seedling, that is at the cotyledon, true leaf, two-leaf or four-leaf stages and the like the treatment is about 0.001 mg to 0.3 mg total active ingredients per plant. This can be accomplished by using a treatment rate of about 0.1 to 200 ppm and preferably 1 to 50 ppm. Use of treatment rates of 300 ppm or greater on young seedlings or young plants, that is prior to the full expansion of the fourth set of primary leaves, will either not cause increases in biomass contemplated by the invention or in many cases, may have a phytotoxic effect on the plant causing it to have stunted growth.

Treatment of perennial trees requires a greater amount of the bioregulator mixture due to the greater mass of the tree. Generally, about one to four grams total active ingredients per tree is applied using a treatment rate of 1 to 100 ppm of bioregulatory mixtures.

The mixtures of the invention may be applied to the plant in any convenient manner. For example, the mixture after being dissolved in water, can be sprayed onto the branches and leaves of the plant. Other application techniques known to the skilled artisan may be employed.

Appropriate wetting agents such as Triton X-100 (polyethylene glycol p-isooctylphenylether made by J. T. Baker), ORTHO X-77 (a mixture of fatty acids, fatty alcohols and isopropanol made by Chevron Chemical Company), Sweep 4F (chlorothalonil from Diamond Shamrock Company) and the like may be added to the aqueous solution to aid in plant treatment. Appropriate penetrating agents such as B-cyclodextrin (B-(heptamer)-cyclodextrin made by Takeda Chemical Industries, Ltd.) or Tween 80 (polyoxyethylene (20) sorbitan monooleate, available from E. Merck, Darmstadt Germany) may be added to the aqueous solution to increase penetration of the bioregulatory compound. Solutions of bioregulator and appropriate wetting agent may be adjusted to an acidic pH (pH 4 to 5) prior to plant application. However, the addition of wetting agent(s) or adjustment of the final bioregulator solution to a specified pH value does not limit the scope of the invention.

Without any intention of limiting the scope of the invention, it is theorized that the compounds comprising the mixtures used in the method of the invention play a role in the photosynthetic pathway in green plants. It is theorized that application of the compounds to the developing green plant causes increased assimilation of carbon dioxide in the photosynthetic pathway thereby increasing the carbon atoms available for synthesis of total biomass and individual plant constituents. It is further theorized that use of the compounds at an early stage of plant or fruit development and before completion of cell differentiation manipulates the genetic expression of the plant so as to tap unused biological potential. Thus as new cells develop under the influence of the bioregulatory compounds, they possess increased capacity to form and store valuable materials and to form an increased amount of plant tissues.

As stated above the mixtures of the invention when applied in accordance with the method of the invention, substantially increase total biomass, enhance the amount of some or all plant constituents and in many cases increase the rate of growth in green plants over untreated plants as long as constituents such as water and light which are necessary for plant growth are present in the required amount.

For example, treated Hamlin, Valencia, and Pineapple sweet orange trees show an accelerated ripening of fruit. When compared with untreated controls, treatment of Citrus trees produces mature fruits that have an increased brix, essential oil, and vitamin C contents. Juice color is increased by chemical treatment. Thus, the method of the invention produces significant improvements in the nutritional and sensory qualities of Citrus products and reduces the time to harvest of mature Citrus fruits. Similar reductions in the days to crop maturation have been observed in a variety of ornamental crop plants (aster, verbena, petunia, pansy). Thus, the methods of the invention may find use on any green plant where increased growth rate, biomass, maturation, or the like is desired. The method is particularly valuable for use on plants which produce food, fiber, energy, or where commercial production of crop plants is limited due to low crop productivity when grown without bioregulator treatments.

EXAMPLE 1

At Republic Groves of Hardee County, Fla. five year-old trees of Hamlin Sweet Orange were treated with the following individual compounds and mixtures in the following concentrations:

DCBTA 10, 50, 100 ppm
MBTA 10, 50, 100 ppm
MBTA/DCBTA mixture 1, 50, 100 ppm each compound All bioregulator solutions contained 0.1% Tween 80 (w/v). All trees received a single foliage application of chemical as a complete canopy spray. Fruit sizes ranged from 9 to 12 mm in diameter at time of chemical treatment. Control trees received a single application of 0.1% Tween 80. Treatments were performed using a Mighty Mac portable electric sprayer. Each treatment consisted of five trees. Mature fruits were harvested from each treatment at 6 months after chemical treatment.

TABLE 1

Promotive effects of tertiary amine bioregulators on fruit development of Hamlin sweet orange.

| Treatment | Fruit Diameter (mm) | Peel Thickness (mm) | Fruit Compositon (%) | | | |
|---|---|---|---|---|---|---|
| | | | Juice | Peel | Pulp + Seeds | TOTAL |
| CONTROL | 67.6 | 3.4 | 51.5 | 38.1 | 7.6 | 97.2 |
| DCBTA-10 | 67.6 | 3.0 | 53.9 | 36.2 | 8.0 | 98.1 |
| -50 | 68.4 | 2.8 | 54.0 | 35.5 | 8.6 | 98.1 |
| -100 | 65.8 | 3.3 | 53.4 | 37.2 | 7.6 | 98.2 |
| MBTA-10 | 66.6 | 3.0 | 54.2 | 35.9 | 8.1 | 98.2 |
| -50 | 67.8 | 2.9 | 54.1 | 35.8 | 8.7 | 98.6 |
| -100 | 66.1 | 3.0 | 54.4 | 35.5 | 9.3 | 99.2 |
| Mix[2] 1/1 | 69.4 | 2.8 | 53.1 | 34.9 | 11.3 | 99.3 |
| 10/10 | 69.2 | 2.2 | 57.9 | 30.5 | 9.9 | 98.3 |

TABLE 1-continued

Promotive effects of tertiary amine bioregulators on fruit development of Hamlin sweet orange.

| Treatment | Fruit Diameter (mm) | Peel Thickness (mm) | Fruit Compositon (%) | | | |
|---|---|---|---|---|---|---|
| | | | Juice | Peel | Pulp + Seeds | TOTAL |
| 50/50 | 68.4 | 3.1 | 56.8 | 33.5 | 9.2 | 99.5 |

[2]Mixture of DCBTA & MBTA, (1 l,w/v)

RESULTS

Figure 1A:
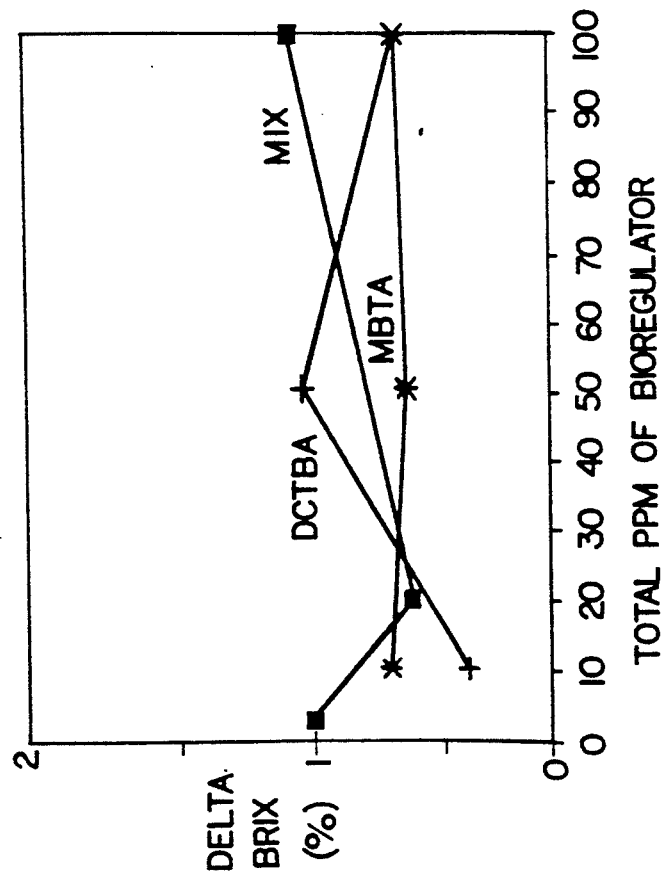
FIG. 1A shows the effect of a mixture of MBTA and DCBTA on Hamlin sweet orange juice brix.
Figure 1D:
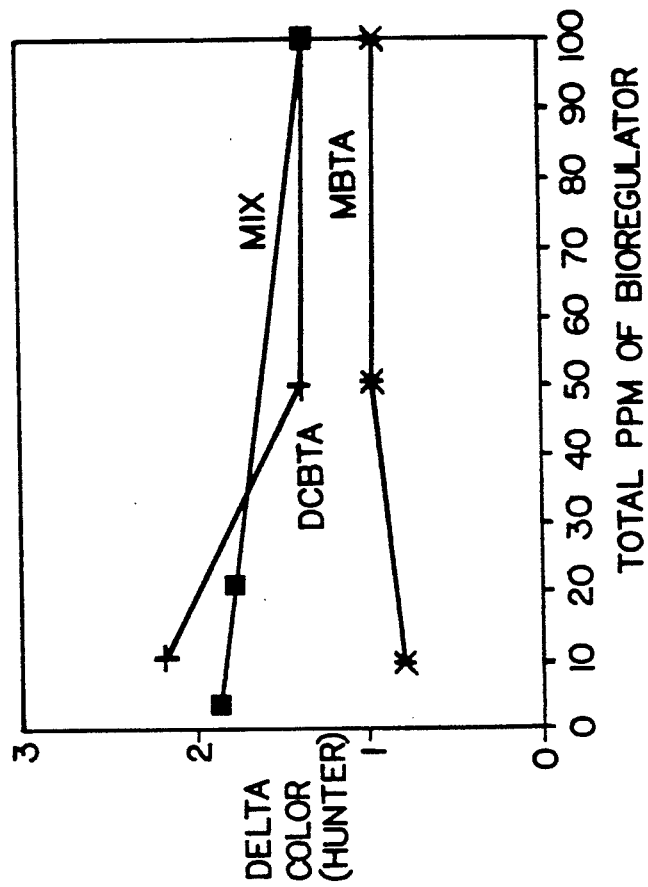
FIG. 1D shows the effect of a mixture of MBTA and DCBTA on Hamlin sweet orange juice color.
Figure 1C:
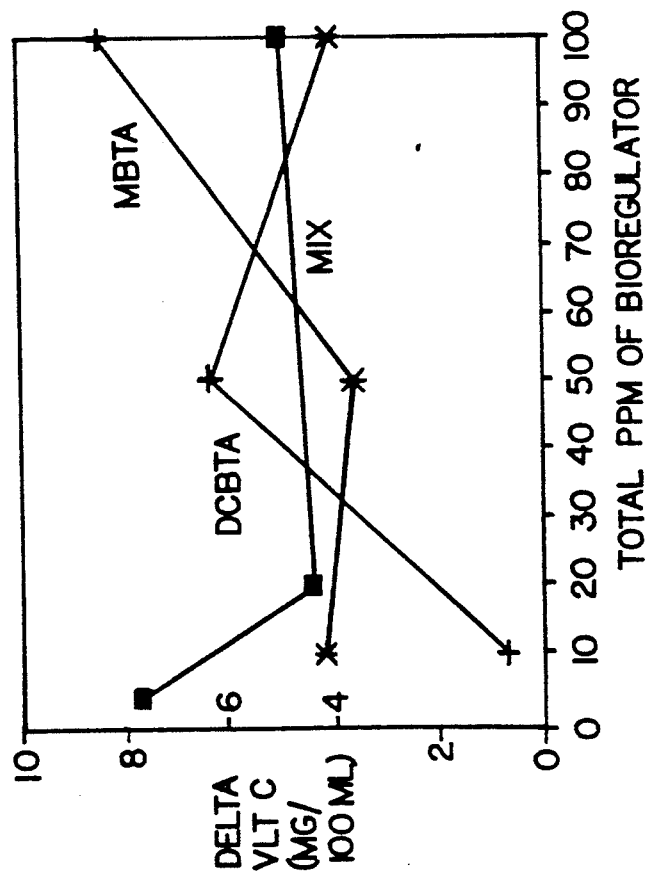
FIG. 1C shows the effect of a mixture of MBTA and DCBTA on Hamlin sweet orange juice vitamin C content.

Application of a mixture of MBTA and DCBTA to Hamlin sweet orange trees at the beginning of fruit growth significantly enhanced the juice content (Table 1) and juice quality (FIGS. 1a-d) of mature fruits when compared with the values of controls. In addition, application of MBTA and DCBTA as single compound treatments significantly enhanced the productivity of mature fruits. Among all treatments, chemical improvements of peel development and juice content (Table 1) were greatest within the MIX 10/10 treatment. Juice quality was determined by the calculation of Delta values (Value$_{delta}$=value$_{treatment}$-value$_{control}$) for juice brix, juice brix to acid ratio (BAR), juice vitamin C content, and juice color (Hunter scale). Among the mixture treatments, the MIX 1/1 treatment showed the largest numerical improvements in juice quality (FIG. 1). In general, the MIX 1/1 treatment showed the largest numerical improvements in juice brix, juice BAR, and juice vitamin C content, when the chemical treatments contained less than 50 ppm bioregulator. Mixture (MIX 1/1 and MIX 10/10) treatments showed intermediate improvements in juice color when compared with 10 ppm MBTA and 10 ppm DCBTA treatments. These results suggest that the biological activities of MIX treatments, when used in low concentrations, are increased relative to the bioactivity of a single chemical treatment. Thus, the use of a mixture of MBTA and DCBTA as foliage treatments allows less chemical to be applied per tree, when compared with single chemical treatments.

We claim:

1. A mixture of chemical compositions suitable for use as bioregulatory agents for plants comprised of a mixture of compounds of the structure:

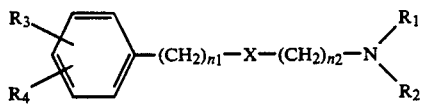

Wherein
X is either oxygen or sulfur,
R$_1$ and R$_2$ are lower alkyl groups containing 1 to 6 carbon atoms, n$_1$ and n$_2$ being integers from 1 to 6, n$_1$ and n$_2$ being independent of each other, with R$_1$, R$_2$, n$_1$, and n$_2$ containing identical or dissimilar chemical structures, R$_3$ and R$_4$ are independently hydrogen, chlorine, bromine, fluorine, iodine, lower alkyl containing 1 to 6 carbon atoms, lower alkoxy containing 1 to 6 carbon atoms, lower alkoxy groups containing 1 to 6 carbon atoms, or condensed mono and polycyclic aromatic ring systems, and wherein:

if R$_3$ and R$_4$ are 3,5,-substituents, then the lower alkyl or alkoxy group must contain 3 to 6 carbon atoms; and wherein:
if R$_3$ is hydrogen, then R$_4$ must be a 4-substituent, with the proviso that R$_4$ is other than hydrogen.

2. The mixture as set forth in claim 1 wherein the mixture is comprised of the compounds N,N-diethylaminoethyl 3,4-dichlorobenzyl ether and N,N-diethylaminoethyl 4-methylbenzyl ether.

3. A method for enhancing plant growth comprised of the steps of applying to a plant a mixture of compounds selected from the group having the structure:

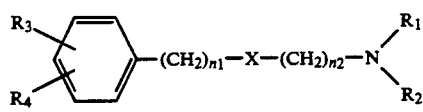

Wherein:
X is either oxygen or sulfur,
R$_1$ and R$_2$ are lower alkyl groups containing 1 to 6 carbon atoms, n$_1$ and n$_2$ being integers from 1 to 6, n$_1$ and n$_2$ being independent of each other, R$_1$, R$_2$, n$_1$, and n$_2$ containing identical or dissimilar chemical structures, R$_3$ and R$_4$ are independently hydrogen, chlorine, bromine, fluorine, iodine, lower alkyl containing 1 to 6 carbon atoms, lower alkoxy containing 1 to 6 carbon atoms, lower alkoxy groups containing 1 to 6 carbon atoms, or
condensed mono-and polycyclic aromatic ring systems, and wherein:
if R$_3$ and R$_4$ are 3,5,-substituents, then the lower alkyl or alkoxy group must contain 3 to 6 carbon atoms; and wherein:
if R$_3$ is hydrogen, then R$_4$ must be a 4-substituent, with the proviso that R$_4$ is other than hydrogen;
or an acid addition salt thereof,
said compounds being applied to the plant immediately prior to or at a time when cell differentiation and growth of the plant or flower buds are great, that is, to the plant seed, the plant seedling prior to the full expansion of the fourth set of primary leaves or to trees during a week before or after flower bud swell, said compounds being applied in an amount to enhance plant growth but not harming the plant and being applied in an amount of approximately 0.001 to 0.3 mg active ingredient per plant seedling or about 0.1 to 4 grams active ingredient per tree, said enhancing of plant growth consisting of an increase in total plant biomass and plant constituents selected from the group consisting of protein, lipid, sugar, and essential oil whereby the compounds biodegrade to elemental form up to four days after application to a plant.

4. The method of claim 3 wherein the mixture is comprised of compound is N,N-diethylaminoethyl 3,4-dichlorobenzyl ether or an acid salt thereof and N,N-diethylaminoethyl 4-methylbenzyl ether or an acid salt thereof.

5. The method of claim 3 wherein the enhancing of plant growth further consists of an accelerated plant maturation and fruit ripening relative to untreated plants.

6. The method of claim 3 wherein the enhancing of plant growth further consists of an increased pigment accumulation relative to untreated plants.

7. The method of claim 3 wherein the plant is a cereal grain.

8. The method of claim 3 wherein the plant is a legume.

9. The method of claim 3 wherein the plant is a citrus tree.

10. The method of claim 9 wherein the fruit of the treated citrus tree exhibits a reduced peel thickness relative to untreated citrus.

11. The method of claim 3 wherein the plant is a vegetable plant, annual or perennial plant, or a plant grown for ornamental purposes.

12. The method of claim 3 wherein the mixture is applied as an aqueous dispersion.

13. The method of claim 3 wherein the mixture is applied to the plant more than once.

14. A method for enhancing plant growth comprised of the steps of applying to a plant a mixture of compounds selected from the group having the structure:

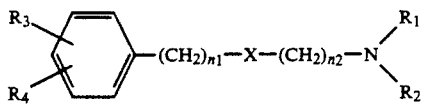

Wherein:
X is either oxygen or sulfur,
$R_1$ and $R_2$ are lower alkyl groups containing 1 to 6 carbon atoms, $n_1$ and $n_2$ being integers from 1 to 6, $n_1$ and $n_2$ being independent of each other, $R_1$, $R_2$, $n_1$, and $n_2$ containing identical or dissimilar chemical structures, $R_3$ and $R_4$ are independently hydrogen, chlorine, bromine, fluorine, iodine, lower alkyl containing 1 to 6 carbon atoms, lower alkoxy containing 1 to 6 carbon atoms, lower alkoxy groups containing 1 to 6 carbon atoms, or condensed mono-and polycyclic aromatic ring systems, and wherein:
if $R_3$ and $R_4$ are 3,5,-substituents, then the lower alkyl or alkoxy group must contain 3 to 6 carbon atoms; and wherein:
if $R_3$ is hydrogen, then $R_4$ must be a 4-substituent, with the proviso that $R_4$ is other than hydrogen; or an acid addition salt thereof.

15. The method of claim 14 wherein the mixture is comprised of N,N-diethylaminoethyl 3,4-dichlorobenzyl ether and N,N-diethylaminoethyl 4-methylbenzyl ether.

16. The method of claim 14 wherein the enhancing of plant growth further consists of an accelerated plant maturation and plant ripening relative to the untreated plant.

17. The method of claim 14 wherein the enhanced plant growth consists of an increased pigment accumulation in leaves and/or fruits relative to the untreated plant.

18. The method of claim 14 wherein the plant is a cereal grain.

19. The method of claim 14 wherein the plant is a legume.

20. The method of claim 14 wherein the plant is a citrus tree.

21. The method of claim 20 wherein the fruit of the treated citrus tree exhibits a reduced peel thickness relative to untreated citrus.

22. The method of claim 14 wherein the plant is a vegetable plant, an annual plant, a perennial plant, or a plant grown for ornamental purposes.

23. A synergistic mixture of compounds suitable for use as bioregulatory agents for plants comprised of N,N-diethylaminoethyl 3,4-dichlorobenzyl ether and N,N-diethylaminoethyl 4-methylbenzyl ether.

* * * * *

UNITED STATES PATENT AND TRADEMARK OFFICE
CERTIFICATE OF CORRECTION

PATENT NO. : 5,304,529
DATED : April 19, 1994
INVENTOR(S) : Yokoyama et al.

It is certified that error appears in the above-indentified patent and that said Letters Patent is hereby corrected as shown below:

```
Column 1, line 7, delete "pending"
Column 1, line 8, delete "pending the" and add --.  The--
Column 1, lines 8-9, change "that application is" to
                  --these applications are--
```

Signed and Sealed this

Seventeenth Day of October, 1995

Attest:

BRUCE LEHMAN

Attesting Officer

Commissioner of Patents and Trademarks